United States Patent
Brown

(10) Patent No.: US 9,278,031 B2
(45) Date of Patent: *Mar. 8, 2016

(54) ADJUSTABLY ATTENUATING EAR PLUG

(71) Applicant: Thomas William Brown, Kansas City, MO (US)

(72) Inventor: Thomas William Brown, Kansas City, MO (US)

(73) Assignee: Brown Innovation, LLC, Lake Quivira, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/339,298

(22) Filed: Jul. 23, 2014

(65) Prior Publication Data

US 2016/0022499 A1 Jan. 28, 2016

(51) Int. Cl.
*A61B 7/02* (2006.01)
*A61F 11/08* (2006.01)

(52) U.S. Cl.
CPC ..................... *A61F 11/08* (2013.01)

(58) Field of Classification Search
CPC ................................................... H04R 25/652
USPC ........................................................... 181/135
See application file for complete search history.

(56) References Cited

U.S. PATENT DOCUMENTS

| | | | |
|---|---|---|---|
| 8,770,338 B1* | 7/2014 | Duncan et al. | 181/135 |
| 8,820,470 B2* | 9/2014 | Brown | 181/135 |
| 2003/0159878 A1* | 8/2003 | Hakansson et al. | 181/135 |
| 2006/0042868 A1* | 3/2006 | Berg et al. | 181/135 |
| 2006/0102418 A1* | 5/2006 | Magidson | 181/135 |
| 2011/0223864 A1* | 9/2011 | Wai | 455/41.3 |

* cited by examiner

*Primary Examiner* — Forrest M Phillips
(74) *Attorney, Agent, or Firm* — Mashburn Law Office, LLC; Donna Denise Mashburn

(57) ABSTRACT

An adjustably attenuating ear plug adapted for use in an ear canal, includes a flexible body, and a valve assembly further comprising a disk and knob translatable relative to the disk, wherein the knob defines at least one inlet, the disk alternately defines at least one shield and hole, and the inlet is alternatively aligned with the hole and shield to varying degrees, so as to selectively and variably expose the canal to the environment.

17 Claims, 5 Drawing Sheets

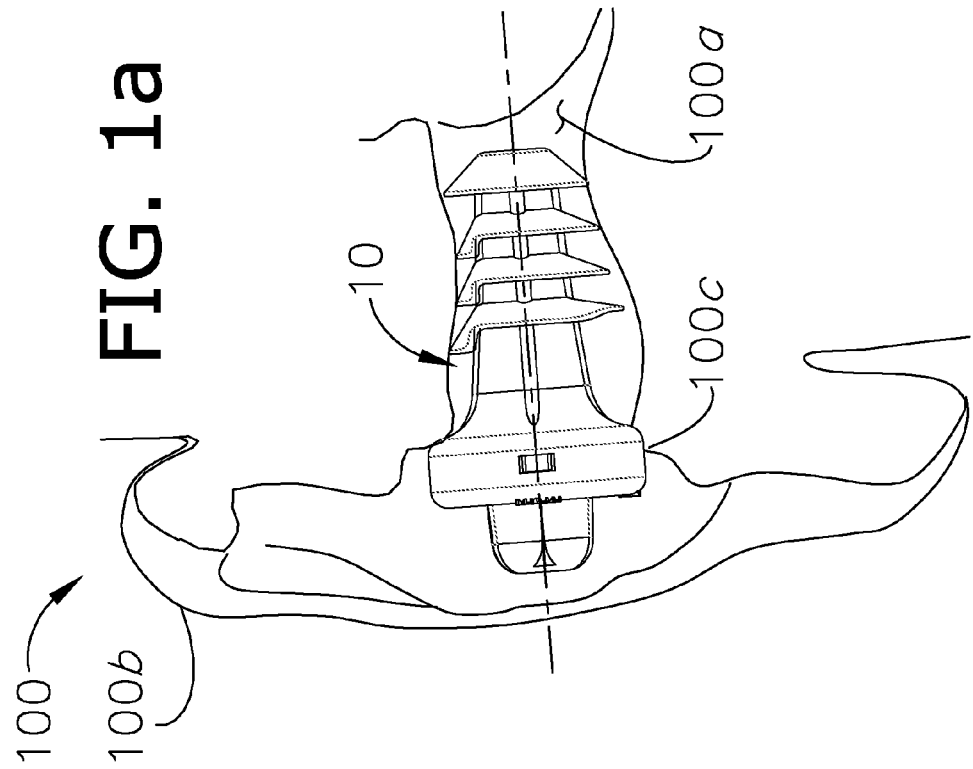
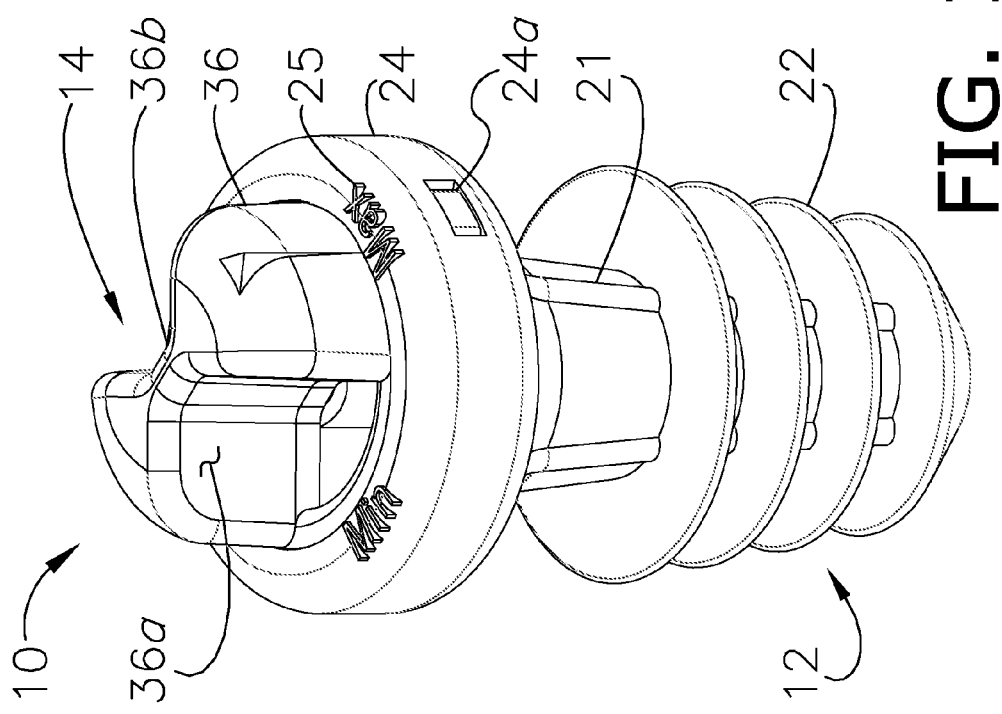

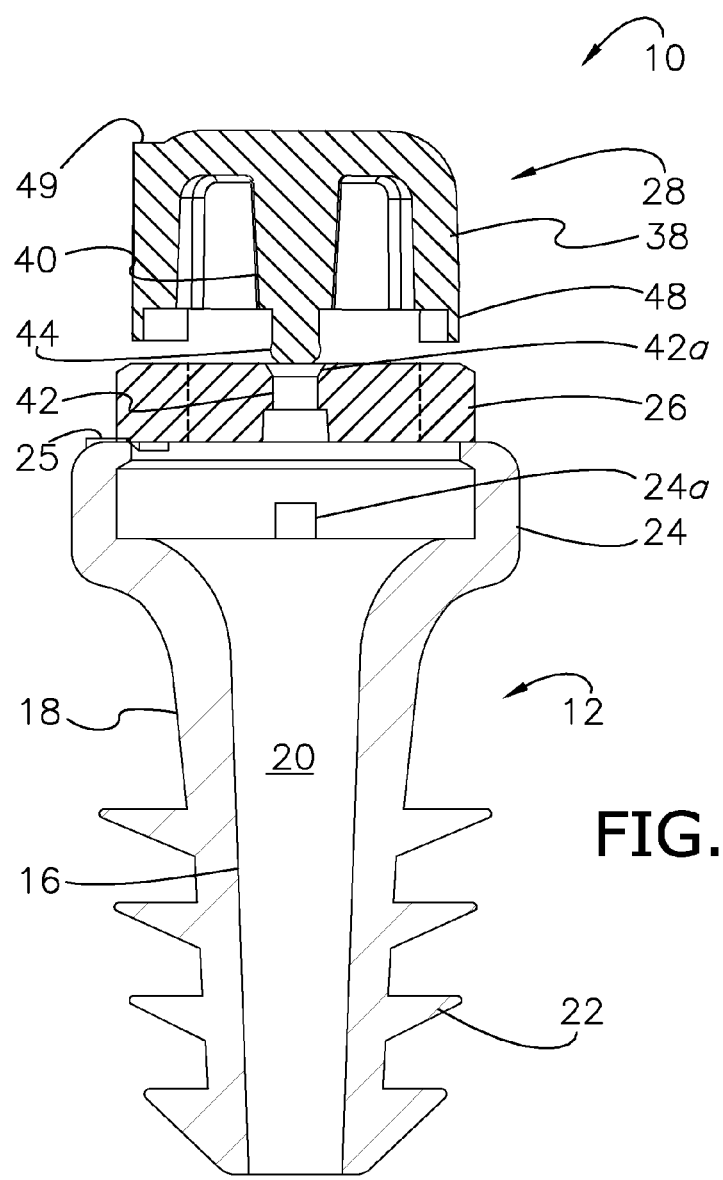
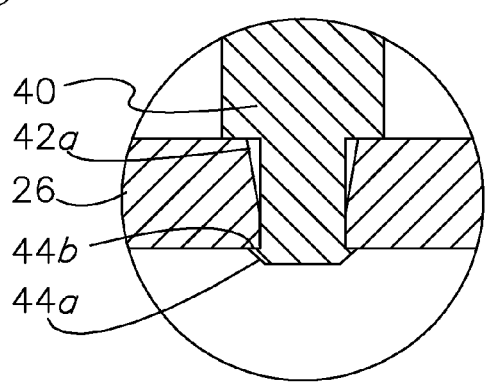
FIG. 3
FIG. 3a

ADJUSTABLY ATTENUATING EAR PLUG

CROSS REFERENCE TO RELATED APPLICATIONS

This application is a continuation of, and claims priority to, U.S. patent application Ser. No. 13/159,740, filed Jun. 14, 2011. U.S. patent application Ser. No. 13/159,740 is incorporated by reference herein in its entirety.

BACKGROUND OF THE INVENTION

1. Field of the Invention

The present invention relates generally to ear plugs, and more particularly, to an ear plug having a manually adjustable valve assembly that enables the attenuation offered by the ear plug to be varied.

2. Discussion of the Prior Art

Though long used to provide auditory attenuation and protection in high decibel or otherwise harmful environments, conventional ear plugs present various concerns in the art, including, for example, typically fixed configurations that offer limited variability. Additionally, current ear plugs are often rectangular in shape, and as such are ill-fitted to the ear canal. Conventional ear plugs typically offer fixed sound attenuation, and must be completely removed from the canal for the user to hear. Adjustable plugs have been developed that offer selective exposure to the canal when in place; however, these measures have relied upon complex and/or cumbersome mechanisms, such as push buttons adjacent the ear, which have also presented various concerns in the art. Push button ear plugs, for example, require an applied force that may cause the plug to further enter the canal undesirably. Thus, there is a need in the art for a more facilely adjustable ear plug that more efficiently reduces sound and engages the canal.

BRIEF SUMMARY OF THE INVENTION

Responsive to these and other concerns, the present invention recites an adjustably attenuating ear plug. The inventive plug is useful for selectively and gradually adjusting the exposure of the ear canal to an ambient environment. The invention is further useful for presenting an ear plug that fits and conforms more securely and comfortably within the ear canal in comparison to prior art ear plugs. Further, the inventive ear plug enables the level of attenuation to be adjusted without removing the ear plug from the canal, and provides an adjustment mechanism that is more facilely manipulated, for example, by dexterously challenged users (e.g., children, elderly, disabled, etc.), in comparison to prior art adjustable ear plugs. The invention is yet further useful for facilitating cleaning and maintenance, so as to increase the life, safety, and effectiveness of the earplug.

In general, the invention concerns an adjustably attenuating ear plug adapted for use at least partially within an ear canal, for manual manipulation by a user, and for selectively exposing the canal to an ambient environment. The ear plug comprises a flexible body defining an elongated shape, a longitudinal tunnel, and internal and external surfaces. The body is configured so as to be at least partially inserted within the canal when the ear plug is donned. The ear plug further comprises a valve assembly communicatively coupled to the tunnel, manually adjustable, and operable to selectively expose the canal to the environment as a result of being manually adjusted.

Other aspects and advantages of the present invention, including the incorporation of a sound collecting surface, and securing conformal vanes, will be apparent from the following detailed description of the preferred embodiments and the accompanying drawing figures.

BRIEF DESCRIPTION OF THE DRAWING FIGURES

A preferred embodiment(s) of the invention is described in detail below with reference to the attached drawing figures of exemplary scale, wherein:

FIG. 1 is a perspective view of an adjustably attenuating ear plug including a valve assembly comprising a knob defining a sound collecting surface, and further including a flexible tubular body having a plurality of conformal vanes and an overarching lip defining lateral openings, in accordance with a preferred embodiment of the invention;

FIG. 1a is an elevation of the ear plug shown in FIG. 1, operatively inserted within an ear canal;

Figure 4A:
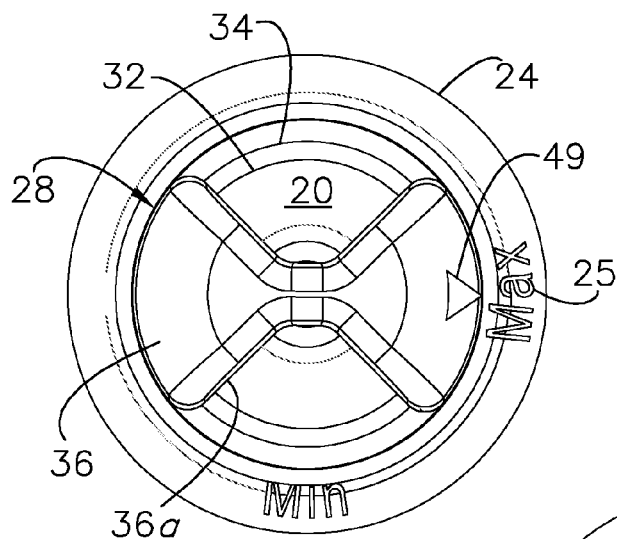
Figure 4B:
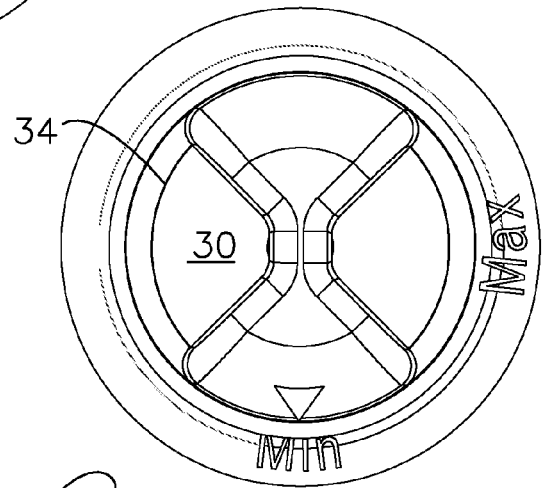
Figure 5:
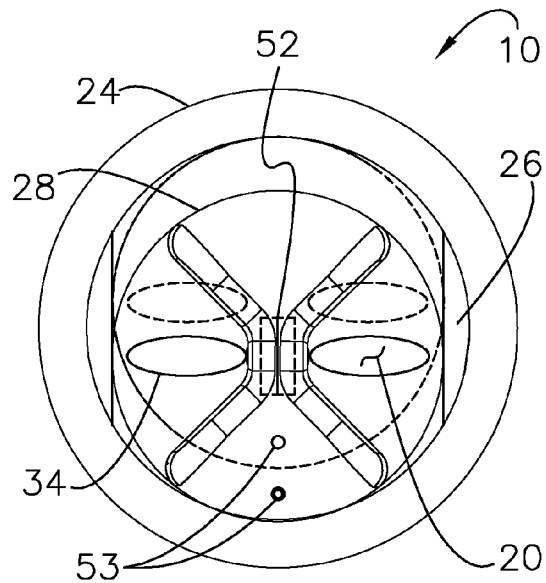
Figure 6A:
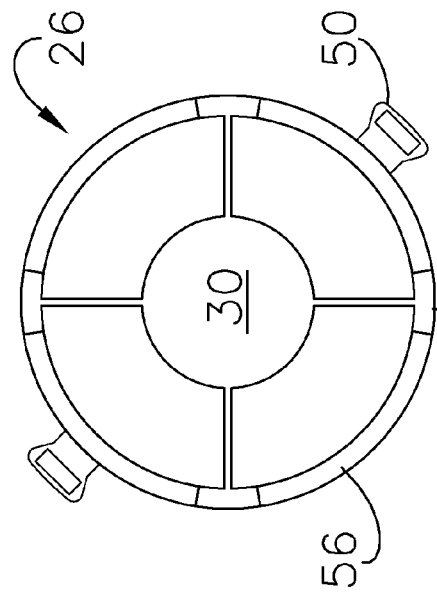
Figure 6B:
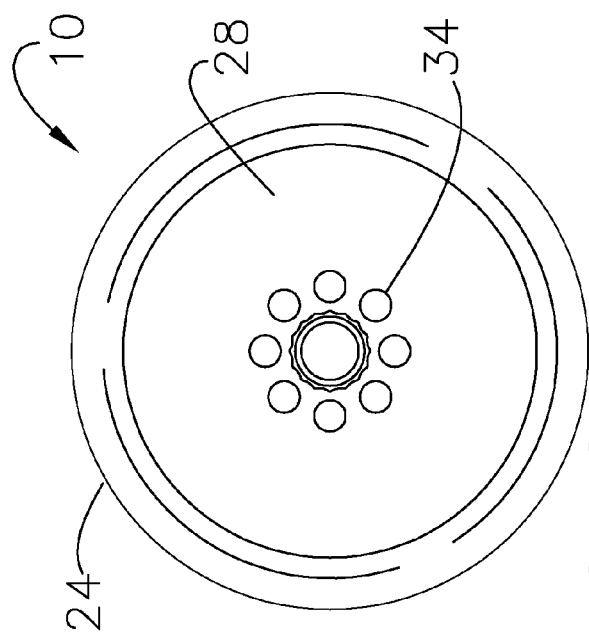
Figure 6C:
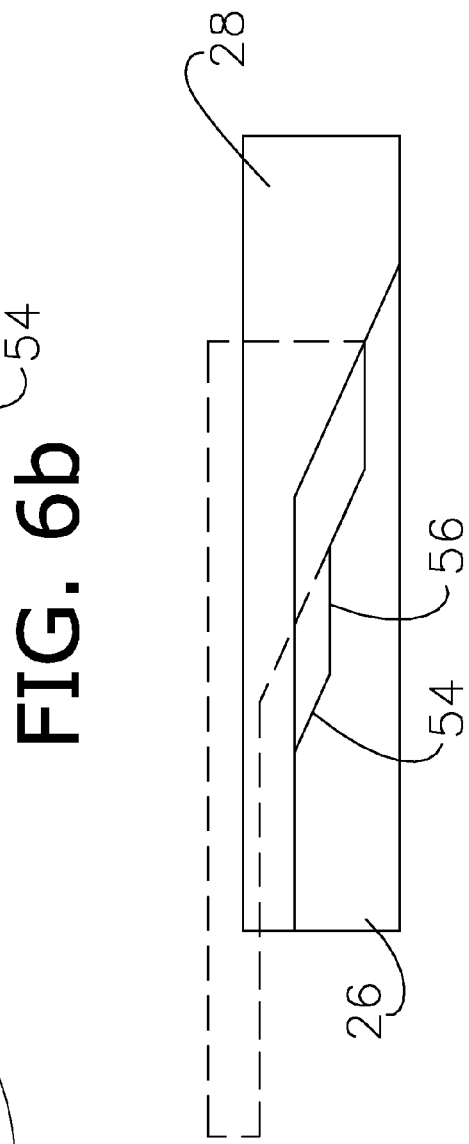

FIG. 3 is a longitudinal cross-section of the ear plug shown in FIG. 1a taken along the longitudinal axis shown therein, particularly illustrating the knob, and a disk coupled with the knob, wherein disk presents opposite radial stubs, and the stubs are inserted within the lateral openings, and further illustrating in enlarged caption, a prong presented by the knob and inserted within a through-hole defined by the disk, in accordance with a preferred embodiment of the invention;

FIG. 3a is a caption view of an alternative prong rib, in accordance with a preferred embodiment of the invention;

FIG. 4a is a top view of the ear plug shown in FIG. 1, wherein first and second inlets defined by the knob and shields defined by the disk are fully aligned, in accordance with a preferred embodiment of the invention;

FIG. 4b is a top view of the ear plug shown in FIG. 1, wherein first and second inlets defined by the knob and holes defined by the disk are fully aligned, in accordance with a preferred embodiment of the invention;

FIG. 5 is a top view of a second embodiment of the invention, wherein the valve assembly includes a sliding knob, in accordance with a preferred embodiment of the invention;

FIG. 6a is a top view of a third embodiment of the invention, wherein the knob defines a plurality of inlets, in accordance with a preferred embodiment of the invention;

FIG. 6b is a planar view of the disk in the third embodiment, in accordance with a preferred embodiment of the invention; and FIG. 6c is a cross-sectional view of the knob and disk shown in FIGS. 6a and 6b, particularly illustrating opposite ramp and landing sections in the sealed and third incremental (shown in hidden-line type) positions.

DETAILED DESCRIPTION OF THE INVENTION

Referring to FIGS. 1-6c, the present invention concerns an adjustably attenuating ear plug 10, generally comprising a flexible body 12 and a valve assembly 14, adapted for use within the ear canal 100a (FIG. 1a) of an ear 100. The ear plug 10 is operable to selectively expose the canal 100a to the environment (e.g., sound waves, gases, fluids, particulate matter, etc.) without removing the ear plug 10 from the canal 100a, and in a preferred embodiment, effects gradual adjustability, improves sound collection, and facilitates dismantling and maintenance. The following description of the preferred embodiments is exemplary in nature and is in no way intended to limit the invention, its application, or uses.

Figure 2:
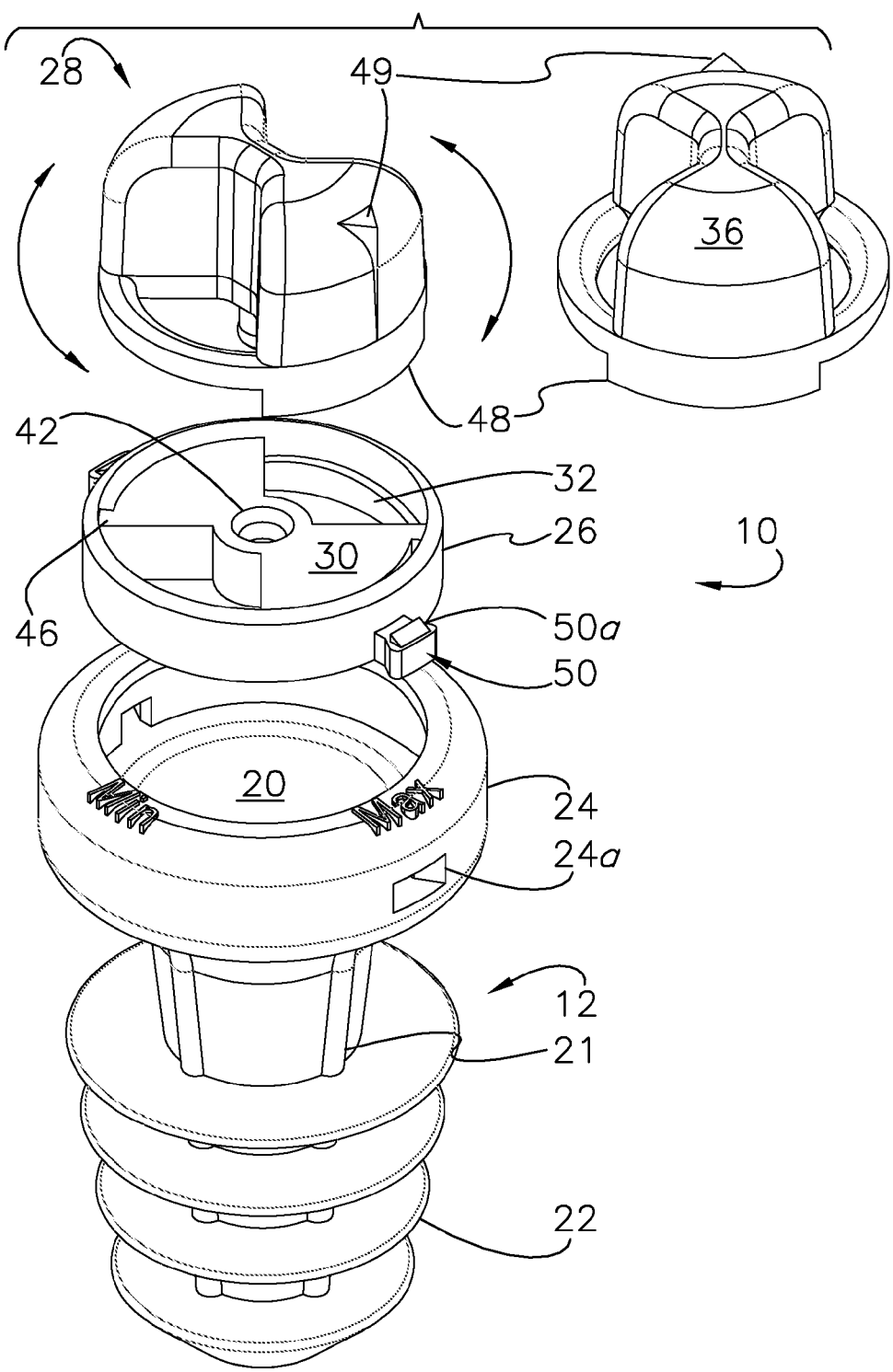
FIG. 2 is an exploded perspective view of an adjustably attenuating ear plug including a valve assembly comprising a knob defining a sound collecting surface, a disk defining alternate shields and holes, and further including a flexible tubular body having a plurality of conformal vanes and an overarching lip defining lateral openings, in accordance with a preferred embodiment of the invention.

As shown in FIGS. 1-3, the flexible body 12 preferably presents an elongated shape, defines internal and external surfaces 16,18, distal and proximal ends, and a longitudinal tunnel 20 as measured along the longitudinal axis (FIG. 1a). In a preferred embodiment, at least the external surface 18 defines a longitudinal taper, so as to more efficiently engage a human ear canal 100a. As shown in FIGS. 1-3, for example, the external surface 18 may define a taper of 5.00°, and have a maximum diameter of 0.323 inches (i.e., 0.820 cm) and a minimum diameter of 0.225 inches (i.e., 0.572 cm). In this configuration, the wall of the body 12 may present a fixed thickness of 0.045 inches (i.e., 0.114 cm), such that the tunnel 20 presents a maximum diameter of 0.223 inches (i.e., 0.566 cm) and a minimum diameter of 0.135 inches (i.e., 0.343 cm). The body 12 is preferably formed of a soft durometer polymer compound, such as, for example, ASTM D2240 type A polypropylene; it is appreciated, however, that various other compounds may be used to form the body 12, including but not limited to a low density polyethylene or polyurethane. As such, the ear plug 10 may be constructed using conventional means, such as injection molding.

As shown in FIGS. 1 and 2, the preferred body 12 further defines at least one, and more preferably, a plurality of evenly spaced longitudinal struts 21 preferably extending from the proximal to the distal end, so as to provide added structural capacity and resistance to torsion.

In the illustrated embodiments, the flexible body 12 defines a plurality of conformal vanes 22 projecting from the external surface 18. The vanes 22 are configured to engage the canal 100a and as such, are preferably oriented orthogonally relative to the longitudinal axis, and present a predetermined diameter correlative to the canal 100a and external surface 18. The vanes 22 are preferably off-centered (i.e., equally spaced) so as to enable full individual conformity. In a preferred embodiment, the vanes 22 each extend from the external surface 18 a distance of 0.066 inches (i.e., 0.168 cm), and present a constant width of 0.026 inches (i.e., 0.066 cm). As such, the vanes 22 preferably present descending outside diameters (e.g., from a maximum diameter of 0.437 inches (i.e., 1.110 cm) to a minimum diameter of 0.360 inches (i.e., 0.914 cm)). When inserted within the ear canal 100a, at least one vane 22 assists the body 12 in engaging and conforming to the canal 100a, so as to secure the plug 10 within the canal 100a.

More preferably, and as shown in FIGS. 1-3, the vanes 22 are sloped rearward, i.e., present sloped leading surfaces as the plug 10 is inserted within the canal 100a, so as to facilitate insertion but deter removal. In this configuration, it is appreciated that the sloped leading surface enables the first vane 22 to be positioned at or near the distal end (FIGS. 1-3). Alternatively, a continuous spiral vane (not shown) may be employed, wherein the plug 10 is twisted during insertion and reversibly so during removal, so as to increase security and facilitate removal.

In the illustrated embodiment, the body 12 defines at the proximal end an overarching lip 24 operable to securely couple the valve assembly 14 to the body 12 (FIGS. 1-3). The preferred lip 24 is elastic and radially compliant, so as to enable insertion and removal of the valve assembly 14. The illustrated lip 24 preferably presents a diameter of 0.590 inches (i.e., 1.499 cm), and arches over the perimeter of the valve assembly 14 by 0.055 inches (i.e., 0.140 cm). More preferably, the lip 24 applies an engaging force to the assembly 14 that further secures it in place, and seals the plug 10. Finally, and as best shown in FIGS. 4a and 4b, it is appreciated that the lip 24 may present indicia 25 conveying, for example, maximum and minimum exposure settings.

In the illustrated embodiment, the valve assembly 14 is comprised of a mated disk 26 and knob 28 (FIGS. 1-6c). The inventive plug 10 employs plural modes of knob translation relative to the disk 26 to effect variable attenuation. Preferably, the valve assembly 14 is formed of a harder material than the body 12 so as to transfer the applied forces and effect the overall function of the ear plug 10; as such, the material composition of the valve 14 may include, but is not limited to, cellulose, metal, or polymers such as polypropylene, polyurethane, polyethylene, or blends thereof. As previously mentioned, the preferred valve assembly 14 is removably coupled to the body 12, so as to facilitate cleaning and maintenance of the ear plug 10.

In a first embodiment, and as best shown in FIGS. 1-4, the disk 26 alternately defines at least one shield 30 and at least one hole 32, and more preferably, a plurality of shields 30 and holes 32. For example, the disk 32 may be divided into radial quarters, wherein the quarters alternatively define the holes 32 and shields 30. FIG. 2 also illustrates the increased thickness of the shields 30 (e.g., 0.050 inches (i.e., 0.127 cm)) compared to the remainder of the disk 26.

As best shown in FIGS. 4a and 4b, the knob 28 preferably defines first and second inlets 34, and includes a head 36 preferably defining a butterfly shaped configuration. The butterfly shaped configuration effects first and second sound collecting surfaces 36a,b. To reduce material, the knob 28 is preferably hollow, and as such, may be generally formed by a outer shell 38 having a thickness of 0.050 inches (i.e., 0.127 cm) and a central prong 40 (FIG. 3). The head 36 is of predetermined height (e.g., 0.225 inches (i.e., 0.572 cm)) and sufficiently extends exterior to the canal 100a to facilitate manual engagement, increase precision, and enable adjustment without pushing the ear plug 10 further into the canal 100a.

To match the disk 26, the knob 28 is generally divided into radial quarters, wherein the quarters alternately define inlets 34 and the wings of the butterfly shaped configuration (FIGS. 4a and 4b). The inlets 34 operate in conjunction with the shields 30 and holes 32 of the disk 26, such that increasing the alignment of the inlets 34 and shields 30 (FIG. 4a) reduces, and increasing the alignment of the inlets 34 and holes 32 (FIG. 4b) increases the exposure of the canal 100a to the environment. As shown, the inlets 34 preferably present areas smaller than the shields 30, so that the shields 30 completely occlude the canal 100a from the environment when the inlets 34 are completely aligned with the shields 30. In a preferred embodiment, the shields 30 and inlets 34 are cooperatively configured to form an inset when fully aligned; that is to say, at least a portion of each shield 30 is inserted within the mouth of the corresponding inlet 34, e.g., as a result of the compressive force applied by the lip 24. It is appreciated that such a configuration may provide haptic feedback to the user, when complete alignment is reached. To facilitate departure from the inlets 34, the shields 30 and/or inlets 34 preferably define rounded or tapered engaging surfaces 34a (FIG. 4a), which enables lifting disengagement to occur as the knob 28 is being rotated.

As previously mentioned, the butterfly shaped configuration of the knob 28 presents sound collecting surfaces 36a,b adjacent the inlet 34 and along the height of the head 36 (FIG. 2). The sound collecting surfaces 36a,b mimic the function of the pinna 100b of the ear 100 by utilizing contours to direct the exposure of the environment (e.g., sound waves) into the inlet 34. More particularly, the curved surface of the sound collecting surfaces 36a,b produces a focal point, and is preferably angled so as to deflect fluid and sound toward the canal 100a. It is further appreciated that the butterfly shaped configuration provides contour to the knob 28 that facilitates manual engagement with the fingertips (not shown) of the user.

As shown in FIG. 3, the knob 28 is coupled to the disk 26 by a prong 40 and through-hole 42 defined respectively thereby. In the illustrated embodiment, the prong 40 defines a bulged rib 44 presenting the maximum prong diameter. In a preferred embodiment, the maximum prong diameter is approximately 0.002 inches (i.e., 0.005 cm) greater than the through-hole diameter, so that the prong 40 is able to manually snap through the through-hole 42. More preferably, the through-hole 42 defines a tapered section 42a that facilitates insertion (FIGS. 3 and 3a). As a result, the disk 26 and knob 28 are pivotally coupled. The rib 44 preferably defines a rounded profile as shown in FIG. 3, so as to enable disassembly by the user. When assembled, the disk 26 and knob 28 correlatively slide and are sealably engaged by the lip 24. Alternatively, the rib 44 may define a tapered wall 44a and lateral face 44b that deters removal (FIG. 3a) and effects a more permanent valve assembly 14.

In the first embodiment, the rotation of the knob 28 relative to the disk 26 is preferably discontinuous. To that end, the disk 26 may define first and second protruding stops 46 (FIG. 2), where the knob 28 defines first and second travel guards 48 (FIG. 2). The guards 48 and stops 46 are alternately positioned and cooperatively configured, so as to be selectively caused to engage one another during, and thereby limit, rotational displacement between the knob 28 and disk 26. The positioning of the stops 46 are such that the maximum rotation of the knob 28 in either direction (i.e., clockwise or counter-clockwise) coincides with the complete alignment of the inlets 34 and holes 32 or the inlets 34 and shields 30. So as to further indicate complete alignment, the preferred knob 28 includes an indicator 49. For example, and as shown in FIGS. 1-3, the indicator 49 may be configured to point to the aforementioned indicia 25, when the knob 28 is in the completely aligned positions.

In a preferred embodiment, the compliant lip 24 further defines first and second lateral openings 24a operable to receive first and second rigid stubs 50 defined by the disk 26, so as to laterally, longitudinally, and angularly further secure the valve assembly 14 relative to the body 12. As shown in FIGS. 4a and 4b, the preferred stubs 50 and openings 24a are diametrically opposite. It is appreciated that a greater plurality of stubs 50 and openings 24a may be utilized for added security. Although the stubs 50 may present a variety of shapes, in the preferred embodiment, they present a reversed trapezoidal configurations defining inwardly tapered lateral walls 50a and a distal base (i.e., an outwardly flared configuration), again for added security. In this configuration, once the stub 50 is pushed through the stretchable opening 24a, the inwardly tapered lateral walls 50a work to deter removal. It is appreciated that the openings 24a may themselves define outwardly flared configurations to facilitate insertion. Alternatively, the stubs 50 may present a spherical shape.

In preferred operation, the user inserts the body 12, distal end first, at least partially into the canal 100a, such that the assembly 14 and lip 24 are pressed against the concha 100c of the ear. When inserted, the flexible body 12 conforms to the canal 100a, aided by the conformal vanes 22 and the taper of the external surface 18. When the knob inlets 34 are either partially or completely aligned with the holes 32 of the disk 26, the sound collecting surfaces 36a,b direct the environment into the inlet 34, so as to expose the canal 100a to the environment. When the user desires to attenuate the exposure, the user manually rotates the head 36 of the knob 28, so as to gradually align the inlets 34 and shields 30; and the degree of attenuation is adjusted by increasing or decreasing the alignment between the inlets 34 and shields 30. When use is complete, the plug 10 is removed by grabbing the plug 10 adjacent the lip 24 and gently pulling outward; alternatively the assembly 14 may be initially removed from the lip 24, so as to allow the body 12 to better fold before pulling outward.

A second embodiment offered by the invention is shown in FIG. 5, wherein the knob 28 translates by sliding relative to the disk 26, so as to selectively align the inlet(s) 34 and hole(s) 32. Here, the user adjusts the attenuation offered by the plug 10 by manually causing the knob 28 to resistively slide preferably within a sealed track 52 to a predetermined position, and varying the degree of alignment as a result thereof. The knob 28 and disk 26 may cooperatively present detents 53 that correspond to the predetermined positions. Otherwise the plug 10 functions similar to the first embodiment, and as such will not be further described herein.

A third embodiment of the inventive ear plug 10 is shown in FIGS. 6a-c, wherein the valve assembly 14 is configured to longitudinally space at least a portion of the knob 28 from the disk 26, and more particularly the inlet(s) 34 from the shield (s) 30. In this configuration, the assembly 14 defines a transmission 54 that converts the rotational displacement of the knob 28 into longitudinal displacement. For example, a series of stair-stepped ramps 56 having landings 58 corresponding to an incremental adjusted position may be defined by the disk 26, while the knob 28 defines a congruent and opposing arrangement (FIG. 6c). The knob 28 defines at least one inlet 34 (FIG. 6a) that engages a circular shield 30 defined by the disk 26 (FIG. 6b). More preferably, the shield 30 is compressible so as to effect sealed engagement with the inlet 34 at least in the lowermost position. Asides from the circular shield 30 and the ring formed by the ramps 56, the disk 26 is generally open (FIG. 6b), such that when the inlet 34 is spaced from the shield 30, a path of ingress is established into the canal 100a. It is appreciated that variably spacing the shield 30 and inlet 34 results in varying the attenuation offered by the plug 10.

In operation, once the plug 10 is positioned securely within the canal 100a, the knob 28 may be rotated to vary the attenuation, wherein rotation in a first direction increases exposure, while opposite rotation decreases the exposure of the canal 100a to the environment. When the angular surfaces are brought to engage in the first direction, the knob 28 is longitudinally spaced from the disk 26. Once a landing 58 is reached, the valve assembly 14 reaches a stable condition. It is appreciated that the applied force produced by the lip 24 causes the knob 28 and disk 26 to remain compressively engaged during use, and more particularly, acts to resist incidental rotation, and hold the assembly 14 in an achieved stable condition.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Also, as used herein, the terms "first", "second", and the like do not denote any order or importance, but rather are used to distinguish one element from another, and the terms "the", "a", and "an" do not denote a limitation of quantity, but rather denote the presence of at least one of the referenced item. All ranges directed to the same quantity of a given component or measurement is inclusive of the endpoints and independently combinable.

What is claimed is:

1. An adjustably attenuating ear plug adapted for use within an ear canal, for facilitating manual manipulation by a user, and for variably exposing the canal to an ambient environment, said ear plug comprising:
   a flexible body defining an elongated shape, a longitudinal tunnel, and internal and external surfaces, and configured so as to be at least partially inserted within the canal when the ear plug is donned; and
   a valve assembly communicatively coupled to the tunnel, manually adjustable, and operable to selectively expose the canal to the environment.

2. The ear plug as claimed in claim 1, wherein the assembly is gradually adjustable, so as to gradually expose the canal to the environment.

3. The ear plug as claimed in claim 1, wherein the flexible body further defines at least one conformable vane projecting from the external surface, and the body is cooperatively configured with the canal such that at least one of said at least one vane is caused to bear against the canal when the ear plug is donned.

4. The ear plug as claimed in claim 1, wherein the body is formed of a soft durometer polypropylene polymer.

5. The ear plug as claimed in claim 1, wherein at least a portion of the body is longitudinally tapered.

6. The ear plug as claimed in claim 1, wherein the valve assembly includes a knob, and a disk slidingly engaged with and translatable relative to the knob, the knob defines at least one inlet, the disk alternatively defines at least one shield and at least one hole, said at least one inlet and hole are selectively alignable, so as to selectively expose the canal to the environment, and said at least one inlet and shield are selectively alignable so as to selectively occlude the canal from the environment.

7. The ear plug as claimed in claim 6, wherein the knob further defines a head of predetermined width extending exterior to the canal, and geometrically configured so as to facilitate manual manipulation, when the ear plug is donned.

8. The ear plug as claimed in claim 6, wherein the flexible body further defines distal and proximal ends, and the proximal end defines an overarching lip sealably engaged with the assembly, and operable to angularly and longitudinally secure the disk relative to the body.

9. The ear plug as claimed in claim 6, wherein the knob linearly translates relative to the disk, and said at least one inlet and hole are selectively aligned as a result thereof.

10. The ear plug as claimed in claim 6, wherein the knob rotates relative to the disk, and said at least one inlet and hole are selectively aligned as a result thereof.

11. The ear plug as claimed in claim 10, wherein the knob and disk cooperatively define a transmission operable to longitudinally space the knob and disk as a result of rotating the knob.

12. The ear plug as claimed in claim 6, wherein the knob defines at least one contoured sound collecting surface adjacent said at least one inlet.

13. The ear plug as claimed in claim 12, wherein the knob defines a butterfly-shaped cross-sectional configuration.

14. The ear plug as claimed in claim 6, wherein the knob includes a prong having a bulged rib defining a maximum prong diameter, the disk further defines a through-hole having a hole diameter less than the maximum prong diameter, and the through-hole and rib are cooperatively configured to be manually snapped together, and pivotally couple the disk and knob.

15. The ear plug as claimed in claim 14, wherein the knob is removably coupled with the disk.

16. The ear plug as claimed in claim 14, wherein the rib defines a tapered wall and laterally extending surface.

17. An adjustably attenuating ear plug adapted for use within an ear canal, for facilitating manual manipulation by a user, and for variably exposing the canal to an ambient environment, said ear plug comprising:
   a flexible body defining an elongated shape, a longitudinal tunnel, and internal and external surfaces, and configured so as to be at least partially inserted within the canal when the ear plug is donned; and
   a valve assembly communicatively coupled to the tunnel, manually adjustable, and operable to selectively expose the canal to the environment,
   wherein the flexible body further defines at least one conformable vane projecting from the external surface, and the body is cooperatively configured with the canal such that at least one of said at least one vane is caused to bear against the canal when the ear plug is donned,
   wherein the valve assembly includes a knob, and a disk slidingly engaged with and translatable relative to the knob, the knob defines at least one inlet, the disk alternatively defines at least one shield and at least one hole, said at least one inlet and hole are selectively alignable so as to selectively expose the canal to the environment, and said at least one inlet and shield are selectively alignable so as to selectively occlude the canal from the environment.

* * * * *